United States Patent [19]
Jawahir et al.

[11] Patent Number: 5,689,062
[45] Date of Patent: Nov. 18, 1997

[54] METHOD OF ASSESSING TOOL-LIFE IN GROOVED TOOLS

[75] Inventors: Ibrahim S. Jawahir, Lexington, Ky.; Xiangdong D. Fang, Keiraville, Australia; Peng X. Li; Ranajit Ghosh, both of Lexington, Ky.

[73] Assignee: University of Kentucky Research Foundation, Lexington, Ky.

[21] Appl. No.: 584,590

[22] Filed: Jan. 11, 1996

[51] Int. Cl.$^6$ .................................................. G01N 3/58
[52] U.S. Cl. ...................... 73/104; 82/1.11; 364/474.17
[58] Field of Search ................ 82/1.11, 173; 408/112, 408/6, 11; 451/1, 2, 21, 28; 409/84, 131, 187; 364/474.17; 73/104

[56] References Cited

U.S. PATENT DOCUMENTS

| | | |
|---|---|---|
| 3,784,798 | 1/1974 | Beadle et al. |
| 4,351,029 | 9/1982 | Maxey et al. |
| 4,547,847 | 10/1985 | Olig et al. |
| 4,559,600 | 12/1985 | Rao |
| 4,707,793 | 11/1987 | Anderson |
| 4,854,161 | 8/1989 | Drits .................................. 73/104 |
| 5,251,144 | 10/1993 | Ramamurthi |

OTHER PUBLICATIONS

Fang, X.D. et al.; The Effects of Progressive Tool–Wear and Tool Restricted Contact on Chip Breakability in Machining;–Wear; 1993; 160; 243–52.

Lau, W.S. et al; The Relationship between Tool Geometry and the Taylor's Tool–Life Constant; International Journal of Mach. Tool Des. Res.; 1989; 20; 29–44.

Dearnley; P.A. et al.; Wear Mechanisms of Coated Carbide Tools; Metals Technology; 1982; 9; 60–75.

Konig, W. et al.; New Approaches to Characterizing the Performance of Coated Cutting Tools; Annals of the CIRP; 1992; 41 (1); 49–54.

Kramer, B.M.; An Analytical Approach to Tool Wear Prediction Ph.D. Thesis; Department of Mechanical Engineering; MIT; 1979.

Usui, E. et al.; Analytical Prediction of Cutting Tool–Wear; Wear; 1984; 100; 129–51.

Venkatesh, V.C. et al.; A Discussion on Tool–Life Criteria and Total Failure Causes; Annals of the CIRP; 1980; 29 (1)–19–22.

ASME, 1985, Tool–life Testing With Single–Point Turning Tools, ASME, New York.

Cook, N.H.; Tool–Wear and Tool–Life; ASME; Journal of Engineering for Industry; 1973; 931–8.

*Primary Examiner*—Daniel W. Howell
*Assistant Examiner*—Kenneth J. Hansen
*Attorney, Agent, or Firm*—King and Schickli

[57] ABSTRACT

A method is provided for assessing tool-wear and predicting tool-life for a selected cutting tool performing a machining operation. The method is broadly defined as including the steps of determining a tool coating effect factor and a chip-groove effect factor for the coated, grooved cutting tool. Additionally, the method includes the calculation of a tool-life for the coated, grooved cutting tool. The method takes into account selected machining operation conditions such as the characteristics of the workpiece material to be cut, the depth of cut, the feed rate, the cutting speed and the cutting tool geometry.

5 Claims, 2 Drawing Sheets

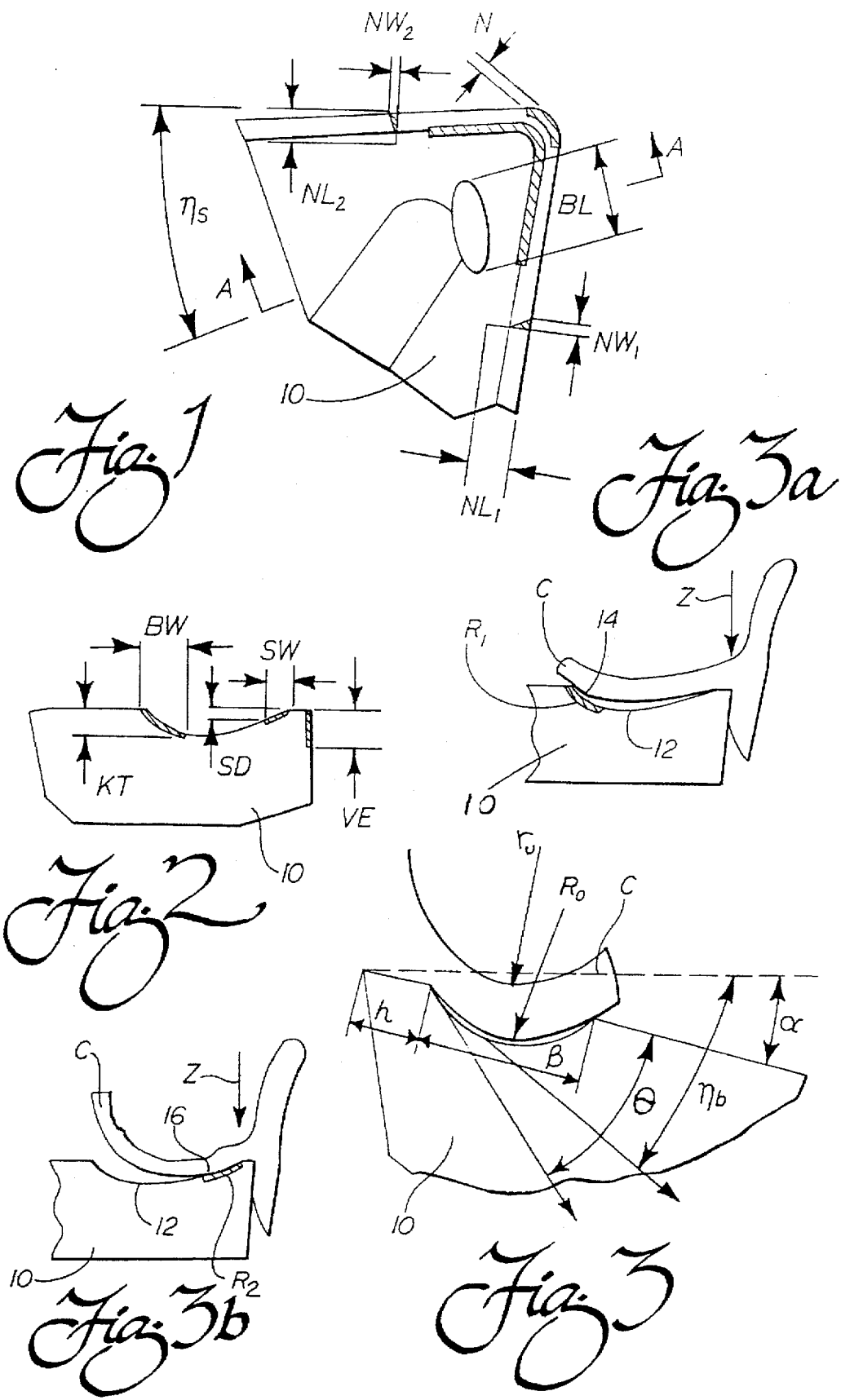

METHOD OF ASSESSING TOOL-LIFE IN GROOVED TOOLS

TECHNICAL FIELD

The present invention relates generally to workpiece machining operations and, more particularly, to a method for assessing tool-wear for a selected coated, grooved cutting tool performing a machining operation.

BACKGROUND OF THE INVENTION

For well over several decades, numerous attempts have been made to develop methods for accurately predicting the effects of machining operations upon a selected cutting tool. Examples of tool-wear/tool-life models are disclosed in, for example, the following:

ASME, 1985, *Tool-life Testing With Single-Point Turning Tools*, ASME, New York;

ISO, 1977, 3685–1977;

Cook, N. H.; Tool-Wear and Tool-Life; ASME; Journal of Engineering for Industry; 1973; 931–8;

Kramer, B. M.; *An Analytical Approach to Tool Wear Prediction*; Ph.D. Thesis; Department of Mechanical Engineering; MIT; 1979;

Usui, E. et al.; Analytical Prediction of Cutting Tool-wear; Wear; 1984; 100; 129–51.

Venkatesh, V. C. et al.; A Discussion on Tool-Life Criteria and Total Failure Causes; Annals of the CIRP; 1980; 29 (1); 19–22; and Lau, W. S. et al.; The Relation Between Tool Geometry and the Taylor's Tool-Life Constant;

International Journal of Mach. Tool Des. Res.; 1989; 20; 29–44.

The effects of mechanical properties in coated tools have also been studied extensively. In these, studies the thermal physical properties of the coatings have been found to significantly contribute to the progressive tool-wear and, therefore, the selection of operating parameters. See, for example, Dearnley, P. A. et al. Wear Mechanisms of Coated Carbide Tools; Metals Technology; 1982; 9; 60–75;

Quinto, D. T.; "Mechanical Property and Structure Relationships in Hard Coatings for Cutting Tools; Journal of Vac. Sci. Tech. A.; 1988; 6 (3); 2149–57; and Konig, W. et al.; New Approaches to Characterizing the Performance of Coated Cutting Tools; Annals of the CIRP; 1992; 41 (1); 49–54.

Further, other studies have shown that chip-forms vary as tool-wear progresses. See for example, Fang, X. D. et al.; The Effects of Progressive Tool-Wear and Tool Restricted Contact on Chip Breakability in Machining; Wear; 1993; 160; 243–52.

While research in tool-wear and tool-life in machining operations has been extensive, methods of tool-life predictability generally suffer from significant inaccuracies. This is due to a number of factors. First, the most commonly utilized criteria are based upon flank wear and crater wear. These criteria often mask the influence of other types of wear such as notch wear on the major and minor edges, nose wear and cutting edge chipping which are all significant factors in tool-wear. Second, all empirical constants for predicting tool-life are predetermined with a wide range (n=0.2–0.3 for carbide tools and n=0.4–0.7 for ceramic tools, etc.). Unfortunately the accuracy and consistency of these values are generally poor. Further, the effects of currently available coatings have not as of this time been fully considered or even been factored into state of the art predictive assessments. Third, almost all currently existing tool-life prediction methods are based on flat-faced cutting tools. As a result, chip flow effects have generally not been considered and, therefore, the variations of the chip breaker configuration have also remained outside the predictive analysis.

A need is therefore identified for an improved method of predicting tool-wear and tool-life for coated grooved tools.

SUMMARY OF THE INVENTION

Accordingly, it is a primary object of the present invention to provide a new and improved method of assessing tool-wear for a selected coated, grooved, cutting tool to be used in performing a specific machining operation overcoming the above-described limitations and disadvantages of the prior.

Still another object of the present invention is to provide a method of accurately predicting the tool-life of a coated, grooved cutting tool used in a machining operation fully taking into consideration tool coating effect and chip-groove effect factors for the cutting tool based upon the characteristics of the workpiece material to be cut, the depth of cut, the feed rate, the cutting speed and the cutting tool geometry.

Still a more specific object of the present invention is to provide a method of predicting tool-life including the determining of chip back-flow angle and chip side-flow angle as well as the measuring and quantifying of groove backwall wear and secondary face wear. Advantageously, the new method is the first to accurately select a cutting tool for optimizing the productivity and minimizing the cost of a machining operation. Further, the method may also advantageously be utilized by tool manufacturers to allow the designing of improved chip-groove geometries for longer tool-life while also maintaining and possibly even improving chip control function.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved method is provided for assessing tool-wear for a selected coated, grooved cutting tool performing a specific machining operation. Generally, the method includes the step of determining a tool coating effect factor $W_c$ and a chip-groove effect factor $W_g$ for the coated, grooved cutting tool. These factors are based upon a number of criteria including the characteristics of the workpiece material to be cut, the depth of cut, the feed rate, the cutting speed and the cutting tool geometry. The method may also be broadly described as including the step of calculating a theoretical tool-life for the coated, grooved cutting tool under selected machining operation conditions.

More specifically describing the method, it includes the step of determining chip back-flow angle and chip side-flow angle for the coated, grooved cutting tool. The method further includes measuring and quantifying the groove backwall wear by width of groove backwall wear BW, length of groove backwall wear BL and depth of groove backwall wear KT. In addition, there is the measuring and quantifying of the secondary face wear by the width of the secondary face wear SW and depth of secondary face wear SD.

In accordance with a still more specific aspect of the present invention, the method of assessing tool-wear is completed in accordance with the formula:

$$T = T_R W_g \left( \frac{V_R}{V} \right)^{W_c \cdot \frac{1}{n}} \quad \text{Equation 1}$$

Where:

T=tool-life;
V=cutting speed;
$T_R$=reference tool-life ($T_R$=1 minute);
$V_R$=reference cutting speed (for 1 minute tool-life);
n=Taylor's tool-life exponent;
$W_c$=coating effect factor; and
$W_g$=chip-groove effect factor.

In accordance with yet another aspect of the present invention, the coating effect factor may be defined by the following formula:

$$W_c = \frac{n}{n_c} \quad \text{Equation 4}$$

where:

n=Taylor's tool-life exponent; and
$n_c$=actual slope modified by coating effect factor determined from actual test of tool-life; and Still further, the chip groove effect factor may be defined by the following formula:

$$W_g = \frac{km}{f^{n_1} d^{n_2}} \quad \text{Equation 5}$$

Where:

f=feed;
d=depth of cut;
m=machining operation effect factor (with m=1 for turning); and
$n_1, n_2$, k=empirical constants.

It should be appreciated that the present method for tool-wear evaluation in machining operations with coated, grooved tools utilizes a parametric approach involving chip-groove features. Advantageously, the present method takes into consideration effects of chip flow, chip-groove features and cutting conditions on progressive tool-wear to provide a more accurate and effective method of predicting tool-life.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated in and forming a part of the specification, illustrates several aspects of the present invention and together with the description serves to explain the principles of the invention. In the drawing:

FIG. 1 is a plan view of a grooved cutting tool illustrating various parameters that are found to contribute to the tool-life;

FIG. 2 is a cross-sectional view taken along line A—A of FIG. 1;

FIG. 3 is a schematical representation illustrating chip back-flow angle;

FIGS. 3a–3c are similar schematical representations illustrating chip back-flow effect for small chip back-flow, large chip-back flow and moderate chip back-flow respectively.

Reference will now be made in detail to the present preferred embodiment of the invention, an example of which is illustrated in the accompanying drawing.

DETAILED DESCRIPTION OF THE INVENTION

It has long been known that tool-life is affected by a combination of a number of measurable tool-wear parameters. The present invention, however, is the first method to fully take into account the effect of chip-groove parameters on the mechanisms or types of tool-wear. Accordingly, the present method starts with the quantification of tool-wear characteristics in grooved tools. Measurable tool-wear parameters for a typical grooved tool 10 as shown in FIGS. 1 and 2 include flank wear VB, width of groove backwall wear BW, length of groove backwall wear BL, depth of groove backwall wear KT, width of secondary face wear SW, depth of secondary face wear SD, nose wear N, notch wear length on main cutting edge $NL_1$, notch wear width on main cutting edge $NW_1$, notch wear length on secondary cutting edge $NL_2$, and notch wear width on secondary cutting edge $NW_2$.

The approximate chip back-flow angle for a given set of cutting conditions may be illustrated with reference to the cross sectional view in FIG. 3. As should be appreciated, a typical grooved tool produces a combination of concurrently occurring tool-wear types including flank wear, crater wear, minor edge chipping and nose wear. Eventual tool failure is attributable to an inner action of these various wear parameters. For example, chip back-flow has a direct effect on the mechanism.

Figure 3C:
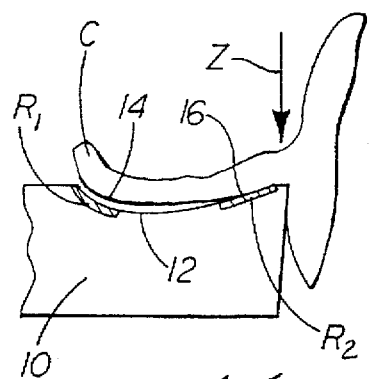

As best shown in FIGS. 3a–3c, different chip back-flow angles also produce different wear mechanisms. For example, a relatively small chip back-flow effect produces wear concentrated in region $R_1$ (see FIG. 3a). In contrast a relatively large chip back-flow angle produces a concentration of wear at substantially the opposite end of the groove identified as region $R_2$ (note, FIG. 3b). In contrast, a moderate chip back-flow angle produces wear at both regions $R_1$ and $R_2$ (note FIG. 3c).

Figure 4A:
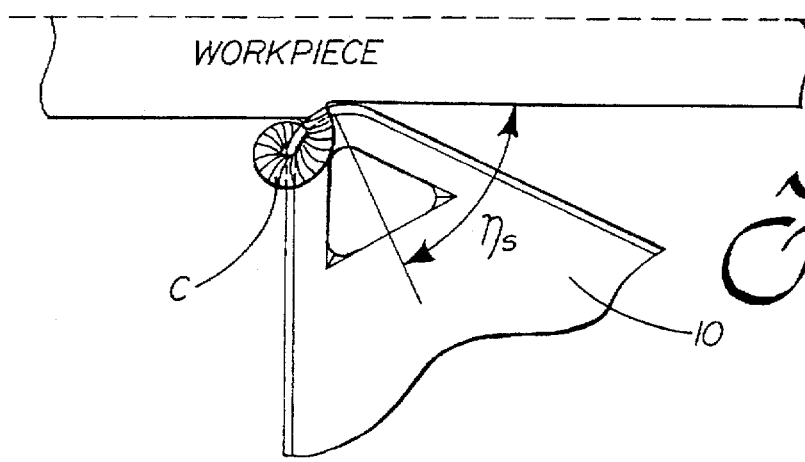
FIGS. 4a and 4b are schematical representations illustrating chip side-flow at relatively small depth of cut and relatively large depth of cut.
Figure 4B:
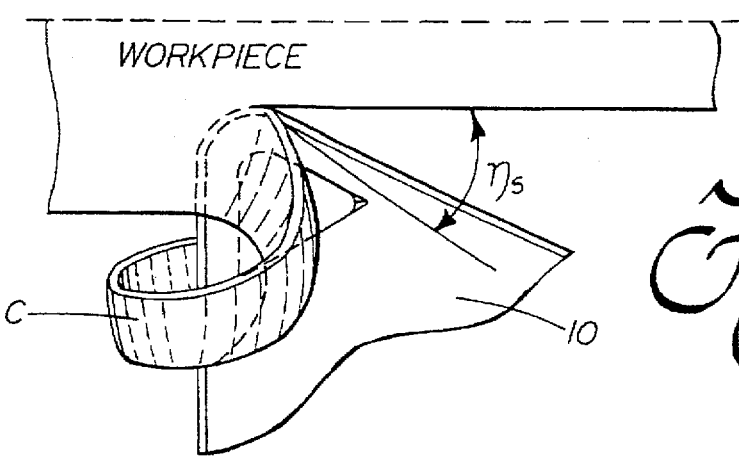

The effects of chip side-flow for depth of cut are best shown in FIGS. 4a and 4b. Chip side-flow at a relatively small depth of cut is illustrated in FIG. 4a. Chip side-flow at a relatively large depth of cut is illustrated in FIG. 4b.

Three-dimensional chip flow in a grooved tool can best be described as occurring with a combined chip side and back-flow. Chip side-flow is in many ways similar to the chip flow characteristics of flat-faced tools. It is chip back-flow, however, that determines the degree of chip streaming into the groove. During machining operations grooved tools produce three-dimensionally curled and broken chips and the flow of these chips has a profound effect on the nature of tool-wear. The most commonly known influencing parameters of three-dimensional chip flow are cutting conditions (feed and depth of cut), chip-groove parameters (toolface land, depth of chip-groove, etc.) and geometry of the groove backwall. In general, for grooved tools a heavy wear load is imposed on a grooved backwall in the radial direction.

At relatively low feeds, the tool/chip natural contact length $h_n$ is less than the toolface land width h. As a result, the chip C neither enters nor is affected by the chip-groove 12 and, accordingly, the tool 10 mimics a flat-faced tool. As the feed increases, however, the tool/chip natural contact length exceeds the toolface land width and the chip C begins to flow into the groove. When the toolface land width is large with respect to the feed, the chip back flow is less and the chip C makes contact with the backwall 14 of the groove. Therefore, in this case, the wear concentrated area is the groove's backwall region (note FIG. 3a). When the feed increase is large, the chip back-flow angle reaches the slope of the groove and the chip tends to flow along the inner-wall of the groove and curls away before reaching the groove backwall. In this case, the toolface land is small with respect to feed and the wear concentrated area is around the tool edge 16 (note particularly FIG. 3b). At moderate feeds and toolface land widths, the cutting edge region 16 and the groove backwall 14 are approximately equally and more uniformally worn (note FIG. 3c). As a result the chip curl is only significantly affected as the tool-wear progresses and this is by far the most favorable mode of tool-wear. In other words, grooved tools should be designed to provide the wear pattern shown in FIG. 3c when used in the application for which the tool has been designed. This, of course, includes basing the tool design on the characteristics of the work material to be cut, the depth of cut, the feed rate and the cutting speed.

As to depth of cut, small depths with respect to the tool nose radius mean that the chip side-flow angle is large. As the depth of cut increases, the effect of the nose radius lessens due to the larger engagement of the straight cutting edge and hence the chip side-flow angle is reduced. Thus, as best shown in FIG. 4a at small depth of cut a large chip side flow angle is provided and the chip C is deflected sidewards resulting in a large chip side-curl. At higher depths of cut, the side-flow angle is less and the chip C is almost fully obstructed by the groove backwall. This produces a mixed up and side-side curl. The chip-burr that is formed at the inner radius of this side-curl chip causes an abrasion-dominated notch wear on the toolface and tool flank surface.

It has also been found that chip breaker configurations have a profound effect on tool-wear and tool-life. Our experiments have shown that different chip forming tool inserts show significantly different tool-wear rates for the same cutting conditions, workpiece material, tool coating and cutting time. This is apparently due to the fact that different chip breaker configurations produce variations in chip flow mechanism.

The three most significant chip-groove parameters that affect tool-wear are toolface land h, depth of chip-groove and the geometry of the groove backwall. As a result, our studies show that the selection of chip-groove designs is very critical and should be matched to the particular application for which the tool is to be utilized in order to provide effective chip breaking and enhanced tool-life. Similarly, the coating used on the grooved tool affects the cutting tool performance and tool-life. Accordingly, a new tool-life relationship is provided that includes a chip-groove effect factor and a tool coating effect factor. Thus, the present method may be broadly described as including the steps of determining a tool coating effect factor $W_c$ and a chip-groove effect factor $W_g$ for a selected coated, grooved cutting tool. These factors are based upon the characteristics of the workpiece material to be cut, the depth of cut, the feed rate, the cutting speed and the cutting tool geometry. Further, the method includes the calculating of a tool-life for the coated, grooved cutting tool under the selected machining operation conditions characteristic of the application for which the tool is to be used.

More specifically describing the method, there is the additional step for determining chip back-flow angle and chip side-flow angle for the coated, grooved cutting tool. This includes the measuring and quantifying of the groove backwall wear by the width of groove backwall wear BW, length of backwall wear BL and depth of backwall wear KT. Further, the method includes the measuring and quantifying of the secondary face wear by the width of secondary face wear SW and depth of secondary face wear SD.

The resulting new tool-life equation utilized in the method of assessing tool-life is in accordance with the formula $$T = T_R W_g \left( \frac{V_R}{V} \right)^{W_c \cdot \frac{1}{n}} \qquad \text{Equation 1}$$

Where:

T=tool-life;

V=cutting speed;

$T_R$=reference tool-life ($T_R$=1 minute);

$V_R$=reference cutting speed (for 1 minute tool-life);

n=Taylor's tool-life exponent;

$W_c$=coating effect factor; and $W_g$=chip-groove effect factor.

In this equation the coating effect factor $W_c$ is quantified first by reference to the basic Taylor's tool-life equation ($VT^n=C$)

$$V_1 T_1^{n_c} = V_2 T_2^{n_c} = C \qquad \text{Equation 2}$$

or $$\frac{V_1}{V_2} = \frac{T_2^{n_c}}{T_1^{n_c}} = \left( \frac{T_2}{T_1} \right)^{n_c} \qquad \text{Equation 3}$$

and $$W_c = \frac{n}{n_c} \qquad \text{Equation 4}$$

where $n_c$ is the actual slope modified by coating effect factor which can be determined from the actual test of tool-life and C is the Taylor's tool-life constant.

A new methodology is also utilized for defining the tool chip-groove effect factor. As shown:

$$W_g = \frac{km}{f^{n_1} d^{n_2}} \qquad \text{Equation 5}$$

Where:

f=feed;

d=depth of cut;

m=machining operation effect factor (with m=1 for turning); and $n_1, n_2$, k=empirical constants.

Substituting Equation 5 into Equation 1, we have $$T = T_R \frac{km}{f^{n_1} d^{n_2}} \left( \frac{V_R}{V} \right)^{\frac{1}{n} W_c} \quad \text{Equation 6}$$

The constants $n_1$, $n_2$, m and k in Equation 6 can be determined through the following procedures.

(a) Determination of $n_1$

The relationship between tool-life and feed can be found by fixing other variables in Equation 6 as follows:

$$T = \frac{C_1}{f^{n_1}} \quad \text{Equation 7}$$

For any combination of feed and tool-life, Equation 7 can be expressed as follows:

$$\frac{T_1}{T_2} = \left( \frac{f_2}{f_1} \right)^{n_1} \quad \text{Equation 8}$$

(b) Determination of $n_2$

Similarly, the relationship between tool-life and depth of cut can be derived by fixing other variables in Equation 6 as follows:

$$T = \frac{C_2}{d^{n_2}} \quad \text{Equation 9}$$

for any combination of depth of cut and tool-life, Equation 9 can be expressed as follows:

$$\frac{T_1}{T_2} = \left( \frac{d_2}{d_1} \right)^{n_2} \quad \text{Equation 10}$$

(c) Determination of m

By assuming m=1 for turning, the machining operation effect factor for different types of operations can be obtained through comparative tests and analysis, as shown below.

Assuming m=1 for turning operations, we have $$m = m_t = \frac{T_t}{T_t} = 1 \quad \text{Equation 11}$$

where $m_t$ is the machining operation effect factor for turning operation and $T_t$ the tool-life for turning operation. Then through the comparative test and analysis, we have, $$m_f = \frac{T_f}{T_t} \quad \text{Equation 12}$$

for a facing operation
and $$m_c = \frac{T_c}{T_t} \quad \text{Equation 13}$$

for a combined turning and facing operation
where:

$m_f$=the value of m for facing;

$m_c$=the value of m for the combined operation of turning and facing;

$T_f$=tool-life for facing; and $T_c$=tool-life for the combined operation of turning and facing.

(d) Determination of k

In order to derive the chip-groove effect factor for different cutting conditions, a reference chip-groove effect factor $(W_g)_R$ first needs to be determined by rearranging Equation 1 as follows:

$$(W_g)_R = \frac{T}{T_R \left( \frac{V_R}{V} \right)^{W_c \frac{1}{n}}} \quad \text{Equation 14}$$

From the results of an actual test of tool-life with a set of reference cutting conditions (e.g. cutting speed=900 sfpm, depth of cut=0.1 in and feed=0.01 ipr), $(W_g)_R$ can be determined using the above equation and k may be obtained by substituting $(W_g)_R$ for $W_g$.

Advantageously, by utilizing the present tool-life equation, it is possible for a given coated grooved tool, workpiece material and tool geometry to predict the tool-life for any given set of cutting conditions (i.e. cutting speed, depth of cut and feed) and any machining operation (turning, facing and combined turning and facing). The following procedure is presented to further illustrate the usefulness of the present method, but it is not to be considered as limited to.

EXAMPLE

Step 1

In this example, the tool coating effect factor $W_c$ is determined for a new coating KC 850. First, a typical set of cutting conditions was selected (depth of cut=0.1 inch, feed=0.01 ipr and cutting speed=1300, 1500, 1700 and 2100 sfpm). The workpiece was a 1037M steel and the grooved tool selected was a CNMG 432 K.

Based upon Equation 3 above, four tool-life tests were conducted at four different cutting speeds and the results are shown in the following table.

TABLE 1

| Tool-life test results for determining coating effect factor $W_c$ | | | | |
|---|---|---|---|---|
| Cutting Speed (sfpm) | 1300 | 1500 | 1700 | 2100 |
| Tool-life (min) | 4.80 | 3.19 | 2.23 | 1.22 |

By plotting the above values on a log-log scale, the value of $n_c$ in Equation 3 was found from the slope of the obtained cutting speed-tool-life relationship (i.e. $n_c$=0.351). Then, based upon Equation 4, the tool coating effect factor $W_c$ was determined by choosing the Taylor's tool-life exponent n=0.25 (for carbide cutting tools). Thus, $W_c$=n/$n_c$=0.25/0.351=0.712.

Step 2

Determination of the chip-groove effect factor $W_g$ for a new grooved tool (CNMG 432 K).

First, the exponent $n_1$ was determined. This was done by choosing the reference cutting speed of 900 sfpm, a reference depth of cut of 0.1 inch, a workpiece of 1037 M steel and a tool coating of KC 850. The exponent $n_1$ was determined based upon equation 8 through the use of a least-square algorithm with three sets of tool-life-feed relationship tests. The tool-life results and the estimated $n_1$ value are shown in Table 2.

TABLE 2

| | Determination of $n_1$ | | |
|---|---|---|---|
| Feed (in/rev) | 0.008 | 0.010 | 0.017 |
| Tool-life (min) | 23.50 | 13.00 | 2.49 |
| $n_1$ | | 3.033 | |

Next, the exponent $n_2$ was determined. This was done by choosing a reference cutting speed of 900 sfpm, a work material (1037 M steel) and a tool coating (KC 850). The exponent $n_2$ was determined based upon Equation 10 also through the use of a least-square algorithm with three sets of tool-life-depth of cut relationship tests. The tool-life results and the estimated $n_2$ value are shown in Table 3.

TABLE 3

| | Determination of $n_2$ | | |
|---|---|---|---|
| Depth of Cut (in) | 0.05 | 0.10 | 0.14 |
| Tool-life (min) | 27.90 | 13.00 | 7.90 |
| $n_2$ | | 1.287 | |

Next the machining operation effect factor m was determined. This was done by choosing a set of reference cutting conditions (cutting speed=900 sfpm, depth of cut=0.1 inch and feed=0.01 ipr) a workpiece of 1037 M steel and a tool coating of KC 850. The tool-life for turning, facing, and combined turning and facing was then obtained respectively through three tool-life tests (i.e. $T_t$=13 minutes, $T_f$=11.7 minutes, and $T_c$=12.35 minutes). This produced the results:

$m=m_t=T_t/T_t=13/13=1$ for turning operation $m=m_f=T_f/T_t=11.7/13=0.9$ for facing operation $m=m_c=T_c/T_t=12.35/13=0.95$ for combined turning and facing operation.

Next, the coefficient k was determined. In order to determine this coefficient, the reference chip-groove effect factor $(W_g)_R$ was first determined. With a set of reference cutting conditions (cutting speed=900 sfpm, depth of cut=0.1 inch and feed=0.01 ipr), the reference chip-groove effect factor $(W_g)_R$ was obtained by substituting the experimental values (i.e. $T=T_r=13$ minutes, $W_c=0.712$, $n_c=0.25$, $T_R=1$ minute, and $V_R=2254$ sfpm) into Equation 14:

Equation 15
$$(W_g)_R = \frac{T}{T_R \left(\frac{V_R}{V}\right)^{w_c \frac{1}{n}}} = \frac{13}{\left(\frac{2254}{900}\right)^{\frac{0.712}{0.351}}} = 0.95$$

Next, the reference chip-groove effect factor $(W_g)_R$ was substituted for the chip-groove effect factor $W_g$ in Equation 5 to obtain the constant k.

$k=(W_g)_R f^{n_1} d^{n_2}=0.95 \times 0.01^{3.033} \times 0.1^{1.287}=4.214 \times 10^{-8}$  Equation 16

Step 3

The Determination of the tool-life equation for chip-groove CNMG 432 K with coating KC 850. The tool-life equation for the new chip-groove CNMG 432 K with coating KC 850 was established through a total of eleven tool-life tests (see Table 4).

TABLE 4

The number of machining tests required to establish a new tool-life equation

| Test | Varying Cutting Conditions/Operations | Referenae Cutting Conditions | Value Determined |
|---|---|---|---|
| 1 | Turning: V = 1300 sfpm | d = 0.1 in<br>f = 0.01 ipr | $W_c$ |
| 2 | Turning: V = 1500 sfpm | d = 0.1 in<br>f = 0.01 ipr | $W_c$ |
| 3 | Turning: V = 1700 sfpm | d = 0.1 in<br>f = 0.01 ipr | $W_c$ |
| 4 | Turning: V = 2100 sfpm | d = 0.1 in<br>f = 0.01 ipr | $W_c$ |
| 5 | Turning: f = 0.008 ipr | V = 900 sfpm<br>d = 0.1 in | $n_1$ |
| 6 | Turning: f = 0.010 ipr | V = 900 sfpm<br>d = 0.1 in | $n_1, n_2,$<br>$(W_g)_R, k$ |
| 7 | Turning: f = 0.017 ipr | V = 900 sfpm<br>d = 0.1 in | $n_1$ |
| 8 | Turning: d = 0.05 in | V = 900 sfpm<br>f = 0.010 ipr | $n_2$ |
| 9 | Turning: d = 0.14 in | V = 900 sfpm<br>f = 0.010 ipr | $n_2$ |
| 10 | Facing | V = 900 sfpm<br>d = 0.1 in<br>F = 0.010 ipr | $m_f$ |
| 11 | Combined Turning and Facing | V = 900 sfpm<br>d = 0.1 in<br>f = 0.010 ipr | $m_c$ |

Thus,

Equation 17
$$T = R_R \frac{km}{f^{n_1} d^{n_2}} \left(\frac{V_R}{V}\right)^{w_c \frac{1}{n}} = \frac{4.214 \times 10^{-8} m}{f^{3.033} d^{1.287}} \left(\frac{2254}{V}\right)^{\frac{0.712}{0.25}}$$

where m=1 for turning operation, m=0.90 for facing operation and m=0.95 for combined turning and facing operation.

In summary, numerous benefits result from employing the concepts of the present invention. The present invention is the first method of assessing tool-wear and predicting tool-life that takes into account the effects of three-dimensional chip flow mechanisms on the tool-wear patterns in grooved tools. This includes consideration of the combined effect of all concurrently occurring tool-wear types such as flank wear, nose wear, notch wear, groove backwall wear and secondary backwall wear. With the ever-growing number of commercially available grooved cutting tools there, of course, is a substantial need for better utilization of cutting tools providing a longer tool-life and more consistent tool-life prediction. This is particularly important for machining process planning and automated machining processes in order to insure the most favorable cutting conditions for uninterrupted machining. This allows a substantial increase in productivity. In addition, the new method may be used by cutting tool manufacturers for designing improved chip-groove geometries capable of providing longer tool-life under appropriate conditions and characteristics of their intended use or application. Further, this can be achieved while maintaining or even improving the chip control function. Thus, the present invention represents a significant advance in the practice.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. In a system having a machine with a tool for cutting a workpiece and a fixture for mounting the workpiece, a method of assessing tool-wear for a selected coated, grooved cutting tool performing a machining operation, said method comprising;

measuring cutting tool geometry including flank wear VB, width of groove backwall wear BW, length of groove backwall wear BL, depth of groove backwall wear KT, width of secondary face wear SW and depth of secondary face wear SD;

determining a tool coating effect factor $W_c$ and a chip-groove effect factor $W_g$ for said coated, grooved cutting tool based upon characteristics of the workpiece material to be cut, depth of cut, feed rate, cutting speed and said measured cutting tool geometry; and calculating a theoretical tool-life for said coated, grooved cutting tool under selected machining operation conditions.

2. The method set forth in claim 1, wherein said method of assessing tool-wear is in accordance with the formula:

$$T = T_R W_g \left( \frac{V_R}{V} \right)^{W_c \frac{1}{n}}$$

Where:

$T$=tool-life;

$V$=cutting speed;

$T_R$=reference tool-life ($T_R$=1 minute);

$V_R$=reference cutting speed (for 1 minute tool-life);

$n$=Taylor's tool-life exponent;

$W_c$=coating effect factor; and $W_g$=chip-groove effect factor.

3. The method set forth in claim 2, wherein $$W_c = \frac{n}{n_c}$$

where $n$=Taylor's tool-life exponent and $n_c$=actual slope modified by coating effect factor determined from actual test of tool-life.

4. The method set forth in claim 2, wherein $$W_g = \frac{km}{f^{n_1} d^{n_2}}$$

where f=feed, d=depth of cut, m=machining operation effect factor; and $n_1$, $n_2$, k=empirical constants.

5. The method set forth in claim 1, further including measuring additional cutting tool geometry including nose wear N, notch wear length on main cutting edge $NL_1$, notch wear width on main cutting edge $NW_1$, notched wear length on secondary cutting edge $NL_2$ and notch wear width on secondary cutting edge $NW_2$.

* * * * *